(12) United States Patent
Yoh et al.

(10) Patent No.: US 8,905,966 B2
(45) Date of Patent: Dec. 9, 2014

(54) MICROJET DRUG DELIVERY SYSTEM

(75) Inventors: Jai-Ick Yoh, Seoul (KR); Tae-Hee Han, Seoul (KR)

(73) Assignee: SNU R & DB Foundation (KR)

(*) Notice: Subject to any disclaimer, the term of this patent is extended or adjusted under 35 U.S.C. 154(b) by 81 days.

(21) Appl. No.: 12/844,977

(22) Filed: Jul. 28, 2010

(65) Prior Publication Data

US 2011/0230826 A1  Sep. 22, 2011

(30) Foreign Application Priority Data

Mar. 16, 2010 (KR) .................... 10-2010-0023210
Jun. 15, 2010 (KR) .................... 10-2010-0056637

(51) Int. Cl.
*A61M 5/30* (2006.01)
*A61M 37/00* (2006.01)
*A61M 5/20* (2006.01)
*A61M 5/315* (2006.01)

(52) U.S. Cl.
CPC ............... *A61M 5/30* (2013.01); *A61M 5/204* (2013.01); *A61M 5/2046* (2013.01); *A61M 5/31511* (2013.01); *A61M 2205/36* (2013.01)
USPC ............... 604/70; 604/68; 604/140; 604/141

(58) Field of Classification Search
CPC ... A61M 5/30; A61M 5/2053; A61M 5/2046; A61M 5/3007; A61M 5/3015; A61M 5/2459; A61M 5/484; A61M 5/19
USPC .............................. 604/68, 70, 150, 145–147
See application file for complete search history.

(56) References Cited

U.S. PATENT DOCUMENTS

| | | | | |
|---|---|---|---|---|
| 6,641,553 | B1* | 11/2003 | Chee et al. ...................... | 604/68 |
| 7,400,940 | B2* | 7/2008 | McRae et al. .................. | 700/266 |
| 2002/0045911 | A1* | 4/2002 | Fletcher et al. ............... | 606/167 |
| 2003/0014014 | A1 | 1/2003 | Nitzan | |
| 2003/0114789 | A1* | 6/2003 | Haar et al. ...................... | 604/69 |
| 2004/0260234 | A1* | 12/2004 | Srinivasan et al. ............. | 604/66 |
| 2009/0129945 | A1* | 5/2009 | Adleff et al. .................... | 417/53 |

OTHER PUBLICATIONS

Viren Menezes, Satyam Kumar, and Kazuyoshi Takayama. "Shock wave drive liquid microjets for drug delivery." Oct. 26, 2009. Journal of Applied Physics, vol. 106.*

Viren Menenzes, Satyam Kumar, and Kazuyoshi Takayama. "Shock wave drive liquid microjets for drug delivery." Oct. 26, 2009. Journal of Applied Physics, vol. 106.*

Jeanne C. Stachowiak et al., "Piezoelectric control of needle-free transdermal drug delivery", Journal of Controlled Release, 2007, pp. 88-97, vol. 124.

(Continued)

*Primary Examiner* — Nicholas Lucchesi
*Assistant Examiner* — Weng Lee
(74) *Attorney, Agent, or Firm* — Cantor Colburn LLP (57) ABSTRACT

The present invention relates to a novel type of a needle-free drug delivery system in which strong energy such as a laser beam is focused inside liquid contained in a sealed pressure chamber to cause bubble growth and the volume expansion in the sealed pressure chamber due to the bubble growth so as to elongate an elastic membrane, so that an instantaneous pressure is applied to a drug solution contained in a drug microchamber adjacent to the elastic membrane to allow the drug solution to be injected in the form of a liquid microjet, thereby enabling the drug solution to rapidly and accurately penetrate into the bodily tissues of the patient.

11 Claims, 7 Drawing Sheets

(56) References Cited

OTHER PUBLICATIONS

Viren Menezes et al., "Shock wave driven liquid microjets for drug delivery", Journal of Applied Physics, 2009, pp. 1-3, vol. 106, No. 086102.

G. N. Sankin, et al., "Interaction between shock wave and single inertial bubbles near an elastic boundary," Physical Review E, 2006, pp. 046304-1-046304-4, vol. 74, The American Physical Society.

Viren Menezes, et al., "Shock wave driven liquid microjets for drug delivery," Journal of Applied Physics, 2009, pp. 086102-1-086102-3, vol. 106, American Institute of Physics.

D. A. Fletcher, et al., "Pulsed liquid microjet for microsugery," Applied Physics Letters, Mar. 26, 2001, pp. 1933-1935, vol. 78, No. 13, American Institute of Physics.

Tae-hee Han, et al., "New Drug Delivery System Based on a Laser-Induced Shockwave," 2010, pp. 67-71, vol. 34, No. 1.

* cited by examiner

*Prior Art*

Fig. 7

*Prior Art*

US 8,905,966 B2

MICROJET DRUG DELIVERY SYSTEM

CROSS-REFERENCE TO RELATED APPLICATIONS

This application claims the benefit of Korean Patent Application Nos. 10-2010-0023210 and 10-2010-0056637, filed on Mar. 16 and Jun. 15, 2010 in the Korean Intellectual Property Office, which are incorporated herein by reference in its entirety.

BACKGROUND OF THE INVENTION (a) Field of the Invention

The present invention relates to a drug delivery system for administering a drug into bodily tissues of a patient, and more particularly, to a novel type of a needle-free drug delivery system in which strong energy such as a laser beam is focused inside liquid contained in a sealed pressure chamber to cause bubble growth and the volume expansion in the sealed pressure chamber due to the bubble growth so as to elongate an elastic membrane, so that an instantaneous pressure is applied to a drug solution contained in a drug microchamber adjacent to the elastic membrane to allow the drug solution to be injected in the form of a liquid microjet, thereby enabling the drug solution to rapidly and accurately penetrate into the bodily tissues of the patient.

(b) Background of the Related Art

In general, a variety of drug delivery systems or methods have been applied as a method for administering a treatment drug into a patient's body in a non-oral manner in a medical field. Among these methods, the most commonly used method is an intracutaneous injection method employing a conventional syringe. However, such an intracutaneous injection method is very effective in that a drug can be directly injected into an internal affected region of a patient, but still entails a great shortcoming in that the patient suffers from an inconvenience of having to feel a pain during the injection. Besides, the intracutaneous injection method encounters many drawbacks in that a wound is caused by the use of a syringe needle, leading to a risk of wound infection, a skilled operator is needed to perform the injection treatment, and in that the re-use of the syringe is difficult, resulting in waste of resources.

Due to the drawbacks of the above-mentioned conventional intracutaneous injection method, many researches have been made to develop a needle-less drug delivery system as a substitute for the conventional intracutaneous injection method. In an attempt to develop the needle-less drug delivery system, there has been proposed a drug delivery system which injects a drug at high velocity in the form of a liquid microjet to allow the drug to directly penetrate into an internal target region through the skin's epidermis.

The research of such a microjet drug delivery system was first attempted in the 1930s. The initial microjet drug delivery system is a very basic drug delivery method using a simple microjet mechanism. The above microjet drug delivery system involves various problems in that there is a risk of cross infection, a splash back phenomenon occurs during the microjet injection, and an accurate penetration depth is difficult to adjust, thereby decreasing reliability. Particularly, since such a conventional microjet drug delivery system still has a disadvantage in that the treatment is accompanied by a considerable pain, it was not widely adopted as an alternative to the conventional intracutaneous injection method.

Figure 6:
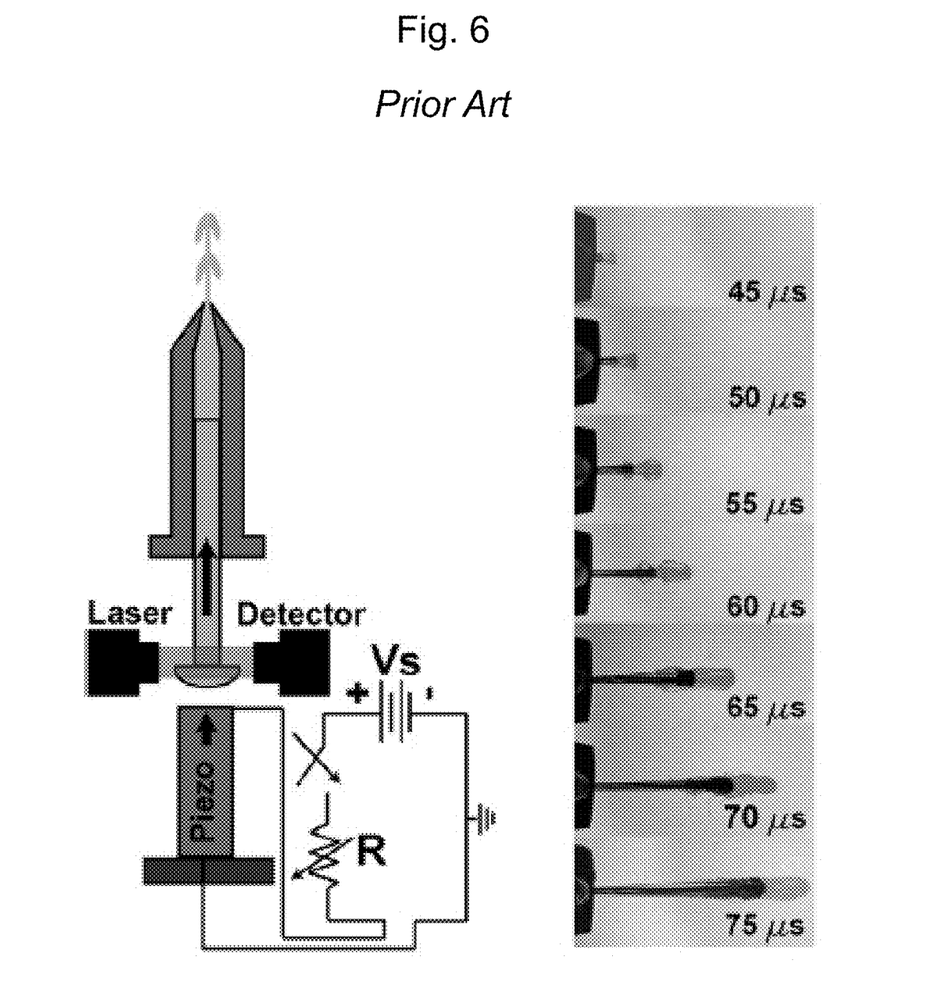
FIG. 6 is a diagrammatic view showing the construction of a conventional microjet drug delivery system using a piezoelectric ceramic element proposed by Stachowiak et al.

In addition, as a method for addressing the pain-related problem involved in the above microjet drug delivery system and stabilize the drug administration, Stachowiak et al. has developed and proposed a microjet drug delivery system using a piezoelectric ceramic element (J. C. Stachowiak et al, *Journal of Controlled Release* 124: 88-97 (2009)). As shown in FIG. 6, the microjet drug delivery system proposed by Stachowiak et al. is one in which a drug is injected at high velocity in the form of a liquid microjet using vibration generated when an electric signal is applied to the piezoelectric ceramic element. According to the microjet drug delivery system to Stachowiak et al., the injected drug can be stably injected intracutaneously into the skin without touching the nervous tissues through a real-time change in injection velocity of the microjet, thereby effectively reducing a pain during the treatment. However, the microjet control of a trace amount of drug must be capable of being performed in order to implement the time-varying monitoring of the drug injection. The microjet drug delivery system using the piezoelectric ceramic element has a great difficulty in realizing an actual drug delivery system due to a limitation of microjet control precision.

Figure 7:
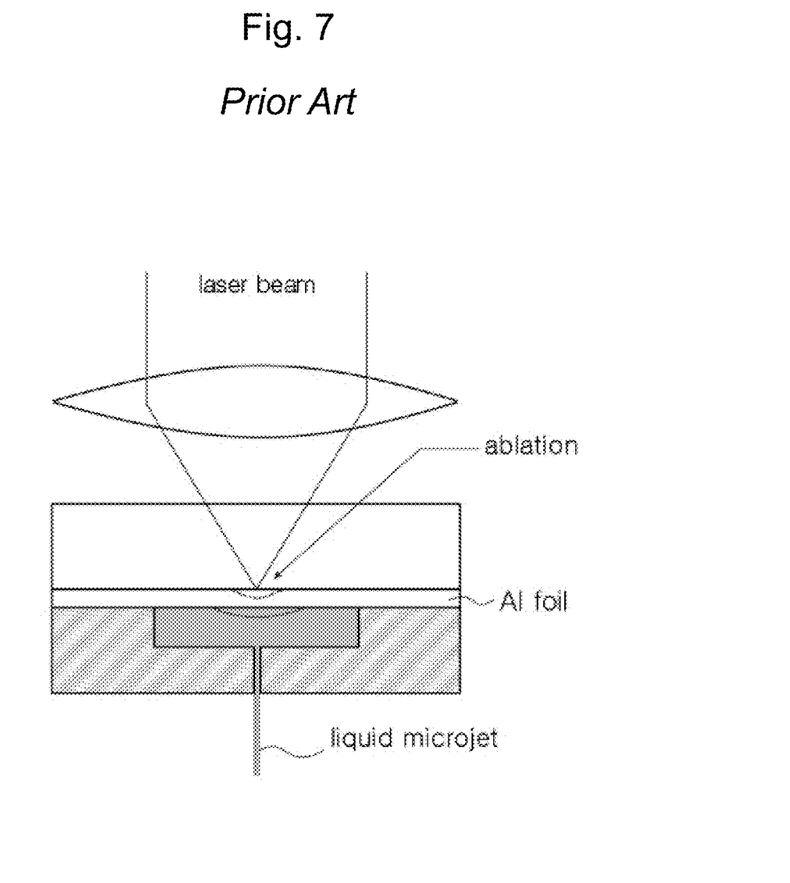
FIG. 7 is a diagrammatic view showing the construction of a conventional microjet drug delivery system using a laser and an aluminum foil proposed by V. Menezes et al.

In the meantime, besides the above microjet drug delivery system using an electric element and device, according to a recent research result, it has been reported that a microjet drug delivery system using a laser was developed (V. Menezes, S. Kumar, and Takayama, *Journal of Appl. Phys.* 106, 086102 (2009)). As shown in FIG. 7, such a microjet drug delivery scheme is one in which a laser beam is irradiated onto an aluminum foil to generate a shock wave so that a drug solution is injected in the form of a microjet. The microjet drug delivery scheme has an advantage in that the laser permits high energy to be focused inside a very small area of the drug solution, enabling implementation of a precise level of needle-free drug delivery system. However, the above microjet drug delivery system using the laser beam and the shock wave entails problems in that continuously controlled microjet injection is impossible, and particularly the re-use of the used system is difficult because ablation occurs on the aluminum foil due to the irradiation of the laser beam thereto.

SUMMARY OF THE INVENTION

Accordingly, the present invention has been made to solve the above-mentioned problems occurring in the prior art, and it is an object of the present invention to provide a novel type of needle-free drug delivery system which injects a drug solution in the form of a microjet to allow the injected drug solution to penetrate into bodily tissues of a patient unlike an existing syringe using a needle, thereby remarkably alleviating a pain of the patient, and is reusable and very advantageous in a hygienic aspect.

Another object of the present invention is to provide a microjet drug delivery system in which since the amount of a drug solution to be injected can be adjusted in the unit of a trace amount, the amount and intensity of a drug to be injected can be freely adjusted on a time-varying basis, and in which since a real-time monitoring is performed easily during the drug delivery, the desired depth and penetration distribution of a drug can be adjusted in the intracutaneous injection of the drug solution.

Yet another object of the present invention is to provide a microjet drug delivery system which enables bubble growth to be caused in a separate pressure-generating liquid (i.e., driving fluid) without directly applying energy for microjet injection of a drug solution, thereby eliminating a risk of damage and deterioration of the drug.

To achieve the above objects, in one aspect, the preset invention provides a microjet drug delivery system which injects a drug solution stored therein in the form a microjet so as to allow the injected drug solution to be penetratingly delivered to bodily tissues of a subject patient, the microjet drug delivery system including: a pressure chamber having a predetermined sealed accommodating space formed therein and configured to store a pressure-generating liquid in the sealed accommodating space; a drug microchamber disposed in proximity to the pressure chamber and configured to accommodate a drug solution in a predetermined accommodating space formed therein; an energy-focusing device configured to focus energy to the pressure-generating liquid stored in the pressure chamber to cause bubble growth due to vaporization of the pressure-generating liquid; an elastic membrane disposed between the pressure chamber and the drug microchamber; and a micronozzle connected to one side of the drug microchamber so as to be formed as a passageway through which the drug solution stored in the drug microchamber is injected to the outside in the form of a microjet.

In the microjet drug delivery system of the present invention, preferably, the energy-focusing device is a laser generator that generates a laser beam and focusably irradiates the generated laser beam onto the pressure-generating liquid stored in the pressure chamber, or an electrode that allows electrical energy to pass therethrough.

According to the microjet drug delivery system as constructed above, a basic concept is adopted in which high energy (for example, laser beam or electric spark) is instantaneously focused inside the pressure-generating liquid contained in the pressure chamber to cause explosive bubble growth in the pressure-generating liquid and the sudden volume increase in the pressure chamber to elongate the elastic membrane so that the drug solution stored in the drug microchamber is injected into bodily tissues such as the human's skin at high velocity into in the form of a microjet through the micronozzle.

That is, for example, the description of the case of using a laser irradiating device as the energy-focusing device will be made hereinafter in brief.

When a laser beam emitted form the laser device is focusably irradiated to the pressure-generating liquid contained in the sealed pressure chamber, there occurs optical breakdown in a liquid molecule structure that receives the focused energy of the laser beam at a focal point portion to cause explosive growth of vapor bubbles. As a result, the entire volume of the contents contained in the pressure chamber increases approximately as many as the volume of the bubbles. Such sudden volume increase forces the pressure-generating liquid contained in the pressure chamber to downwardly pressurize the elastic membrane so that it is elastically elongated to the drug microchamber.

The elongation of the elastic membrane causes a considerable pressure to be instantaneously applied to the inside of the drug microchamber, so that the drug solution stored in the drug microchamber is pressurized and is injected in the form of a liquid microjet through the exit of the micronozzzle.

Thus, in the present invention, the adequate selection of the output, pulse duration and wavelength of the laser beam enables easy control of the microjet velocity so that it is possible to obtain the jet velocity and strength proper to penetrate the skin tissue of a patient to permeate into the patient's body.

In addition, the vapor bubbles generated by the laser beam after the microjet injection of the drug solution vanish immediately together with the termination of the irradiation of the laser beam. As a result, the elastic membrane can be restored to its original state by its elasticity for the standby of the next injection. In this case, according to a preferred embodiment of the present invention, when the drug reservoir becomes in fluid communication with the drug microchamber, the supply of a new drug dose from the drug reservoir to the drug microchamber is automatically performed in response to the restoration of the elastic membrane to its original state immediately after the microjet injection, enabling a successive microjet injection.

Like this, according to the present invention, an innovated microjet mechanism is provided in which a laser beam is not directly irradiated to a to-be-injected drug solution, but is irradiated to the pressure-generating liquid as a separate intermediate medium to cause the explosive growth of the bubbles and the sudden volume increase in the pressure chamber containing the pressure-generating liquid to elongate the elastic membrane, so that the laser beam can act as a pressure source causing the microjet injection of the drug solution. According to microjet drug delivery system of the present invention, laser energy is not directly transmitted to the drug solution, but is transmitted to the drug solution in the form of a microjet injection pressure through the elongation of the elastic membrane, thereby effectively preventing deterioration of the drug solution due to laser heat.

That is, the elastic membrane, which is made of an elastic material such as rubber, functions as a pressure-generating means and functions to protect the drug solution from laser heat or electric heat owing to its relatively low heat conductivity. Further, the immediate supply of a drug solution is resumed in response to the elastic restoration of the elastic membrane immediately after the microjet injection so as to enable smooth consecutive injection. Thus, since the elastic membrane plays an important role in accomplishing the object of the present invention, it is one of most key constituent elements in implementation of the technical concept of the present invention.

According to the drug delivery system of the present invention, unlike an existing syringe using a needle, since a drug solution is injected in the form of a liquid microjet to penetrate bodily tissues of a patient so as to remarkably alleviate a pain of the patient during the medical treatment and the system is reusable and very advantageous in a hygienic aspect, it is expected to be effectively substituted for a conventional drug delivery system using a syringe.

In addition, the drug delivery system of the present invention, an external force is not directly applied to a drug solution to be injected, but laser energy is focused inside a separate pressure-generating liquid to induce the creation of explosive growth of vapor bubbles and the sudden volume increase in the pressure chamber to elongate the elastic membrane adjacent to the pressure chamber in the injection of the drug solution so as to indirectly inject the drug solution, so that a novel type of microjet drug delivery system can be implemented in which there is no risk of damage and deterioration of the drug solution.

Moreover, according to the drug delivery system of the present invention, since a change in the strength and wavelength of the laser beam or the control of voltage enables the adjustment of the to-be-injected drug solution in the unit of a trace amount, a time-varying microjet drug delivery system can be implemented in which the amount and injection strength of the drug to be injected is freely adjusted on a time-varying basis. Consequently, the real-time monitoring and control of the microjet injection is facilitated during the delivery of the drug so that the desired depth and penetration distribution of the drug in the intracutaneous injection of the drug solution.

BRIEF DESCRIPTION OF THE DRAWINGS

The above and other objects, features and advantages of the present invention will be apparent from the following detailed description of the preferred embodiments of the invention in conjunction with the accompanying drawings, in which.

DETAILED DESCRIPTION OF THE PREFERRED EMBODIMENT

The operational mechanism and the technical concept of the microjet drug delivery system will be described hereinafter in more detail in connection with a preferred embodiment with reference to the accompanying drawings.

Figure 1:
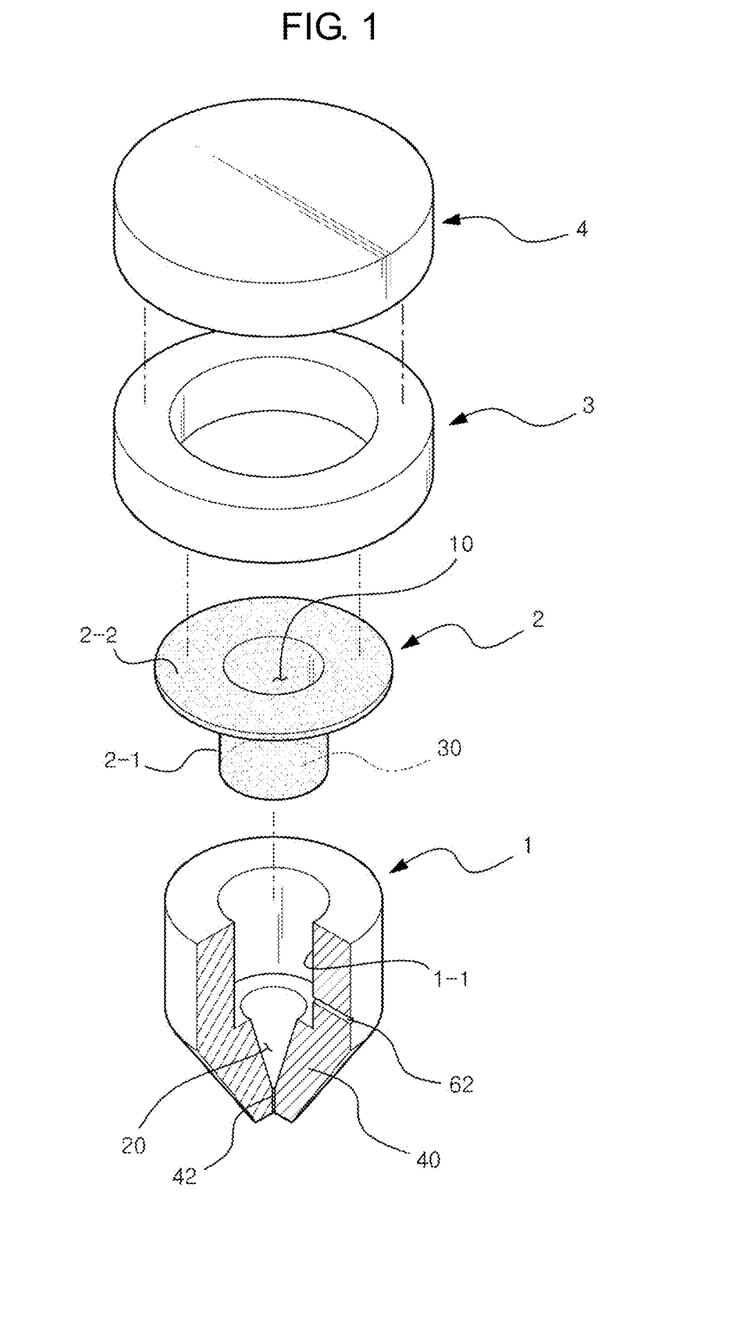
FIG. 1 is a partially cut exploded perspective view showing the technical concept of a microjet drug delivery system according to a preferred embodiment of the present invention.

FIG. 1 is a partially cut exploded perspective view showing the technical concept of a microjet drug delivery system according to a preferred embodiment of the present invention.

Figure 2:
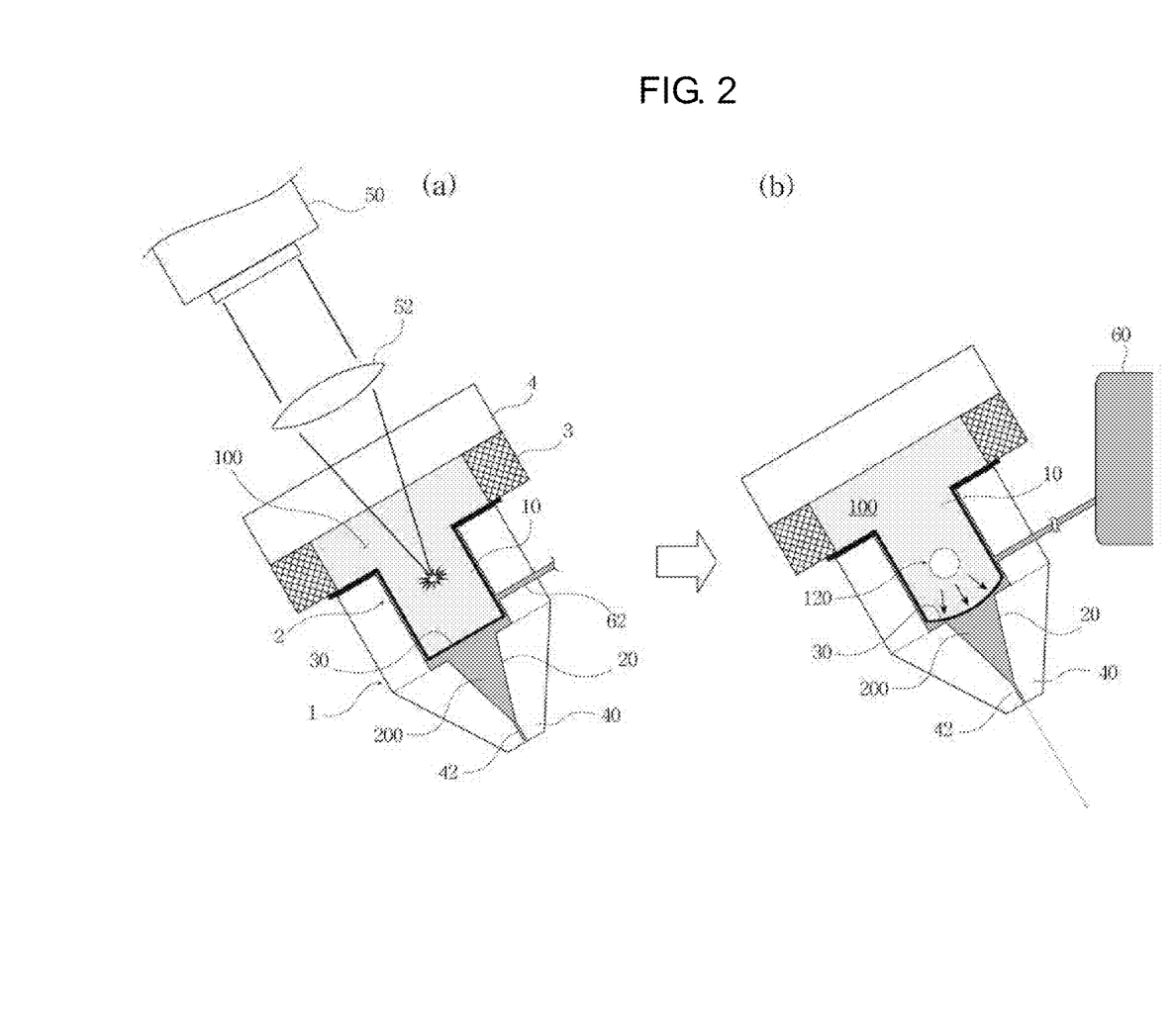
FIG. 2 is a diagrammatic view showing a state in which respective constituent elements of an entire drug delivery system according to the present invention are assembled and coupled to each other and an operational mechanism of the drug delivery system.
Figure 5:
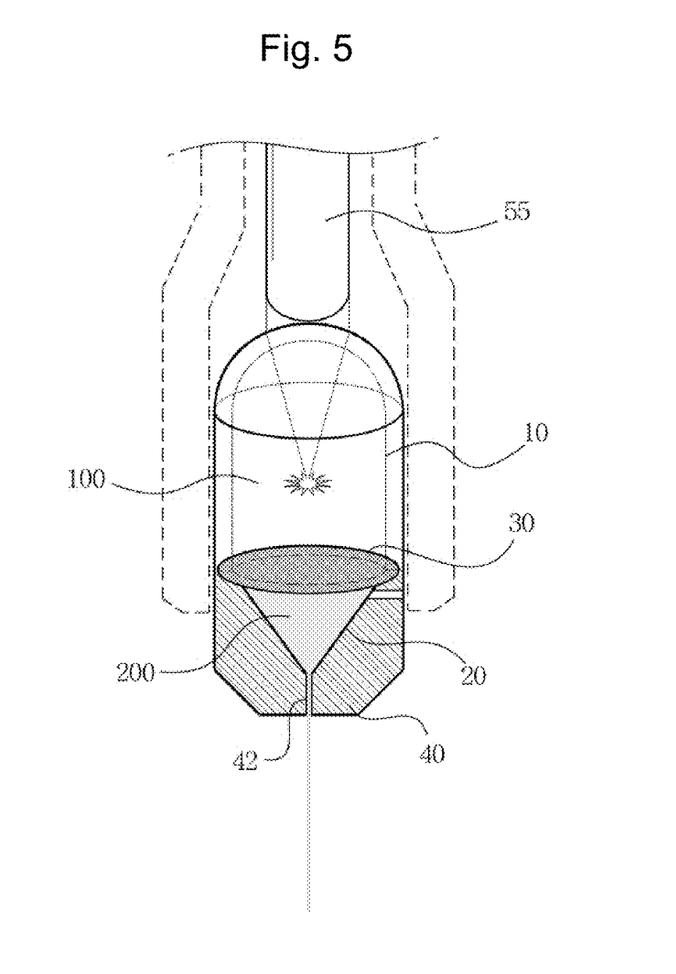
FIG. 5 is a diagrammatic view showing a microjet drug delivery system according to another preferred embodiment of the present invention.

As shown in FIG. 1, the microjet drug delivery system of the present invention basically includes a pressure chamber 10 having a predetermined sealed accommodating space formed therein and configured to store a pressure-generating liquid 100 in the sealed accommodating space; a drug microchamber 20 disposed in proximity to the pressure chamber and configured to accommodate a to-be-injected drug solution 200 in a predetermined accommodating space formed therein; an elastic membrane 30 disposed between the pressure chamber 10 and the drug microchamber 20; a laser device 50 as a energy-focusing device that is configured to generate a laser beam and focusably irradiates the generated laser beam onto the pressure-generating liquid 100 stored in the pressure chamber; and a micronozzle 40 connected to one side of the drug microchamber 20 so as to be formed as a passageway through which the drug solution stored in the drug microchamber is injected to the outside in the form of a microjet. As shown in FIGS. 2 and 5, the energy-focusing device may be disposed separately and outside from the sealed accommodating space of the pressure chamber 10.

Particularly, in this embodiment, it can be understood that two modules are fabricated and assembled with each other as shown in FIG. 1 in substantially constructing the pressure chamber 10, the drug microchamber 20, the elastic membrane 30 and the micronozzle 40, which are main constituent elements for implementation of the technical concept of the present invention.

That is, according to a preferred embodiment shown in FIG. 1, a micronozzle housing module 1 and an elastic chamber module 2 are fabricated and assembled with each other in such a fashion that the elastic chamber module 2 is fitted into the micronozzle housing module 1 so as to constitute an entire drug delivery system. The micronozzle housing module 1 includes the drug microchamber 20 having a to-be-injected drug solution stored therein and the micronozzle 40 connected to the drug microchamber 20, which are fabricated as a single unit. The elastic chamber module 2 includes the pressure chamber 10 and the elastic membrane 30. In this case, according to the preferred embodiment shown in FIG. 1, the pressure chamber 10 is configured to define a sealed internal space together with a separate holder 3 and a cap plate 4 made of a transparent material. In the meantime, although a laser device for irradiating a laser beam is not concretely shown in FIG. 1, such a laser generator may employ a medical Nd:YAG laser equipment or the like which is widely well-known in the art.

As shown in FIG. 1, in this embodiment, the micronozzle housing module 1 includes the drug microchamber 20 formed therein so as to store a drug solution to be injected. At a front end side of the drug microchamber 20 is formed the micronozzle 40 as a passageway through which the drug solution is injected to the outside in the form of a microjet therethrough.

In this embodiment, the micronozzle housing module 1 employs a tungsten carbide material, and may be fabricated by selecting various materials such as other sorts of metals, metal alloy materials, synthetic resin materials or the like within a range of not affecting the accomplishment of the functions of the present invention.

As shown in FIG. 1, the drug microchamber 20 is formed in a tapered shape which is gradually reduced in diameter as it goes toward a front end thereof connected to the micronozzle 40. This is intended to allow a drug solution to be smoothly concentrated to the micronozzle exit 42 so as to be discharged to the outside when a pressure is applied to the elastic membrane 30. In this embodiment, the drug microchamber 20 has the largest diameter of 2.4 mm at a rear end thereof. The micronozzle exit 42 has an inner diameter of 125 µm. In addition, the drug microchamber 20 has a tapered inner angle of 32°, and the drug microchamber 20 fabricated in such a manner can accommodate about 6 µl of a drug solution.

Meanwhile, the micronozzle 40 may include an exit 42 having a coating layer (not shown) formed on the inner peripheral surface thereof. In this case, the coating layer of the micronozzle more preferably uses polytetrafluoroethylene (PTFE) commonly known by trademark name Teflon. The application of the Teflon coating layer considerably decreases the frictional coefficient between the drug solution discharged from the exit and the nozzle surface. Particularly, since Teflon is a strong hydrophobic material, the surface tension between the nozzle surface and the liquid is very small. Such application of the Teflon coating layer can help improve the operating efficiency of the microjet injector of the present invention.

Also, as shown in FIG. 1, the drug microchamber 20 may be constructed such that it includes a drug supply channel 62 formed at one side thereof so as to fluidically communicate with an external drug reservoir 60 (not shown in FIG. 1) so that it can be continuously supplied with a drug from the drug reservoir. The external drug reservoir stores a sufficient amount of drug solution to be injected. When the drug solution contained in the drug microchamber 20 is injected and exhausted, a drug solution is supplied to the drug microchamber 20 from the external drug reservoir through the drug supply channel 62 so as to replenish the drug microchamber 20 with the newly supplied drug solution. The drug reservoir 60 is preferably constructed as a pressure tank so that when the drug microchamber 20 is partially empty after the microjet injection of the drug solution, the drug solution can be automatically pushed and supplied to the drug microchamber 20 along with restoration of the elastic membrane 30 which will be described later. The drug reservoir 60 may separately include other pressure means such as a micropump. Coupled to the rear end of the micronozzle housing module 1 as constructed above is the elastic chamber module 2 as another module for implementing the drug delivery system of the present invention. The elastic chamber module 2 is fabricated to include the pressure chamber 10 and the elastic membrane 30 which are main constituent elements of the present invention, and its concrete shape is as illustrated in FIG. 1.

As can be seen from the embodiment shown in FIG. 1, the elastic chamber module 2 consists of an internally hollow cylindrical piston head 2-1 to define the pressure chamber 10 at the front end thereof, and a flange 202 integrally connected to the rear end of the piston head 2-1 so as to have a shape resembling approximately a hat in its entirety.

Moreover, the micronozzle housing module 1 includes an elastic chamber connecting section 1-1 formed at the rear end side thereof so as to allow the piston head 2-1 of the elastic chamber module 2 to be fitted thereto so that the micronozzle housing module 1 can be coupled with the elastic chamber module 2. The elastic chamber connecting section 1-1 is preferably formed to have an inner diameter slightly greater than an outer diameter of the piston head 2-1 so that when the piston head 2-1 is fitted into the elastic chamber connecting section 1-1, a clearance is created laterally between the piston head 2-1 and the elastic chamber connecting section 1-1 to allow the drug solution supplied through the drug supply channel 60 to be introduced into the drug microchamber 20. Also, the elastic chamber connecting section 1-1 is preferably formed to have a margin depth of approximately 4.5 mm upon insertion of the piston head 2-1 into the elastic chamber connecting section 1-1 so that pressure is smoothly applied to the drug solution contained in the drug microchamber 20 owing to the elastic elongation of the elastic membrane 30 which will be described later upon the generation of bubbles.

Besides, as shown in FIG. 1, according to this embodiment, the elastic chamber module 2 is made of a single material in its entirety so that a circular bottom surface of the piston head 2-1 is formed as the elastic membrane 30. According to this embodiment, the pressure chamber 10 and the elastic membrane 30 can be fabricated as a single member by only once molding operation in the actual fabrication of the elastic chamber module 2, which is very advantageous in terms of the convenience of the fabrication and the fabrication cost. Alternatively, it is to be, of course, understood that the remaining portion of the elastic chamber module 2 except the elastic membrane 30 may be molded of a synthetic resin, or other embodiments of the elastic chamber module 2 may be implemented.

According to this embodiment, the elastic chamber module 2 is fabricated from a thin rubber material in its entirety. More specifically, the elastic chamber module 2 is fabricated from a base nitrile butadiene rubber (NBR) material having a thickness of 200 μm, a hardness of 53, an ultimate strength 101.39 kg/cm$^2$, and an elongation of 449.79%. The NBR material was selected in consideration of flexibility as well as failure in passage of liquid molecules through the elastic chamber module 2. Also, the NBR material can avoid transfer of heat and shock wave to the drug solution to minimize a damage of drug molecules owing to its relatively low heat conductivity.

FIG. 2 is a diagrammatic view showing a state in which respective constituent elements of an entire drug delivery system according to the present invention are assembled and coupled to each other and an operational mechanism of the drug delivery system.

As shown in FIG. 2, it can be seen that the piston head 2-1 of the elastic chamber module 2 is coupled to the elastic chamber connecting section 1-1 of the micronozzle housing module 1 so that the elastic membrane 30 is positioned between the pressure chamber 10 and the drug microchamber 20 so as to partition the pressure chamber 10 and the drug microchamber 20 as two separate compartments.

In the meantime, according to the embodiment shown in FIG. 2, an internally hollow holder 3 is coupled to the rear end of the flange 2-2 of the elastic chamber module 2, and a cap plate 4 is coupled to the rear end of the holder 3, so that a sealed pressure chamber 10 is defined by a space limited by the piston head 2-1 of the elastic chamber module 2, the holder 3 and the cap plate 34. In this case, in this embodiment, the holder 3 and the cap plate 4 are fabricated to have a thickness of 3 mm. In addition, the cap plate 4 can be most preferably made of BK7 glass as a material which is suited to allow a laser beam to pass therethrough without any loss and does not affect volume change of the liquid contained in the pressure chamber 10, heat and the like. Alternatively, the cap plate 4 may be sufficiently made of other materials such as other kinds of glass or transparent acrylic.

Further, according to the present invention, the thus defined pressure chamber 10 is configured to be internally filled with a pressure-generating liquid 100 in a hermetically sealed state. The pressure-generating liquid 100 may be liquid, various liquid-phase materials such as sol or gel, which can receive laser energy from the laser device 50 and cause bubble growth. Various sizes of bubbles may be produced depending on the viscosities of these liquids and the intensity of laser energy, and thus one of ordinary skill in the art will be able to properly select the kind of the pressure-generating liquid and the laser output depending on the concrete product design In this embodiment, pure degassed water is used as the pressure-generating liquid 100 filled in the pressure chamber 10 so as to minimize the remaining bubbles before and after the laser irradiation and microjet injection. As the pressure-generating liquid 100, various liquid-phase materials may be used which includes other alcohol or high molecular sol or gel such as polyethylene glycol. In addition, if water-soluble electrolyte (for example, salt) is added to pure water as the pressure-generating liquid 100, heat energy necessary for optical breakdown in water is reduced due to ionization of water molecules, so that stronger energy can be used for sudden volume increase accordingly, thereby further improving efficiency.

In the meantime, in this embodiment, used as the laser device 50 is a general Q-switched Nd:YAG pulse laser which is widely used currently as a medical laser equipment. A visible laser beam emitted from a Q-switched Nd:YAG pulse laser has a wavelength of 532 nm, a pulse duration of 5-9 ns, and a frequency of 10 Hz. The 532 nm wavelength was obtained through an experiment by selecting one of the output wavelengths of an existing laser equipment. It can be, of course, contemplated that a wavelength of 1064 nm as another output wavelength of the same laser equipment is used or a wavelength of 2900 nm exhibiting the highest energy absorption capability in water is employed. A BK Piano Convex Lens having a focal distance of 10 nm is used as the objective lens 52 used to condense and focus the laser beam.

FIG. 2 is a diagrammatic view showing a state in which respective constituent elements of an entire drug delivery system according to the present invention are assembled and coupled to each other and an operational mechanism of the drug delivery system;

Now, the basic operational principle of the drug delivery system of the present invention as constructed above will be described hereinafter in brief with reference to FIG. 2.

As mentioned above, the drug delivery system according to the present invention employs a laser beam or electrical energy as a basic energy source for microjet injection instead of directly applying physical pressure to the drug solution to inject the drug solution. In this case, the drug delivery system is implemented such that the laser beam is not directly irradiated onto the drug solution to be injected, but the laser beam is focusably irradiated to liquid contained in a separate sealed pressure chamber to cause bubble growth and the volume expansion in the sealed pressure chamber due to the bubble growth so as to elongate the elastic membrane, so that an instantaneous pressure is applied to the drug solution contained in a drug microchamber adjacent to the elastic membrane to allow the drug solution to be injected in the form of a liquid microjet through the micronozzle.

That is, as shown in FIG. 2(a), when a laser beam emitted from the laser device 50 is focusably irradiated to the pressure-generating liquid 100 contained in the sealed pressure chamber 10 via the objective lens 52, there occurs optical breakdown in a liquid molecule structure that receives the focused energy of the laser beam to cause explosive growth of vapor bubbles 120.

The growth of vapor bubbles 120 are produced in the sealed pressure chamber 10 to cause sudden volume increase of the pressure-generating liquid 100 as shown in FIG. 2(a) to allow the elastic membrane 30 to be pressurized outwardly. As a result, an instantaneous pressure is applied to the drug solution 200 contained in a drug microchamber 20 adjacent to the elastic membrane 30 to allow the drug solution 200 to be injected at high velocity in the form of a liquid microjet through the exit 32 of the micronozzle.

The vapor bubbles vanish immediately after the supply of the laser energy is suspended, and thus the elastic membrane is restored to its original state by its elasticity. Subsequently, the supply of the drug solution to the drug microchamber 20 from the external drug reservoir 60 is resumed so that a secondary microjet injection can be consecutively performed.

Particularly, as described above, the present invention enables successive microjet injection of a trace amount of drug solution. In addition, the velocity and strength of the microjet is easily controlled through the adjustment of the wavelength and energy intensity of the laser beam. For this reason, the use of such characteristics of the present invention enables implementation of microjet injection, which makes the time-varying control possible. The implementation of the time-varying microjet injection can be very usefully applied to the medical treatment of pain-free drug delivery. That is, at an initial stage of the microjet injection, the microjet injection of a drug is performed to the extent in which a damage is partially given to the human's skin surface tissues so as to form a drug delivery channel in the skin. At a next stage, the microjet injection of a drug is performed in a relatively low injection rate as compared to the initial stage. That is, if the microjet injection of the drug is controlled at a proper velocity and strength to the extent in which the injected drug penetrates into the skin but does not reach the nervous tissues under the dermis, transdermal drug delivery can be accomplished without causing any pain to a subject patient.

In the meantime, although it has been described in the embodiment illustrated in FIGS. 1 and 2 that a laser device is used as an example of an energy focusing device for focusing energy to the pressure-generating liquid or driving liquid to cause explosive growth of vapor bubbles, the energy focusing device may be implemented as an electric electrode capable of applying electrical energy to the pressure-generating liquid and may be implemented using other types of energy sources.

Figure 3:
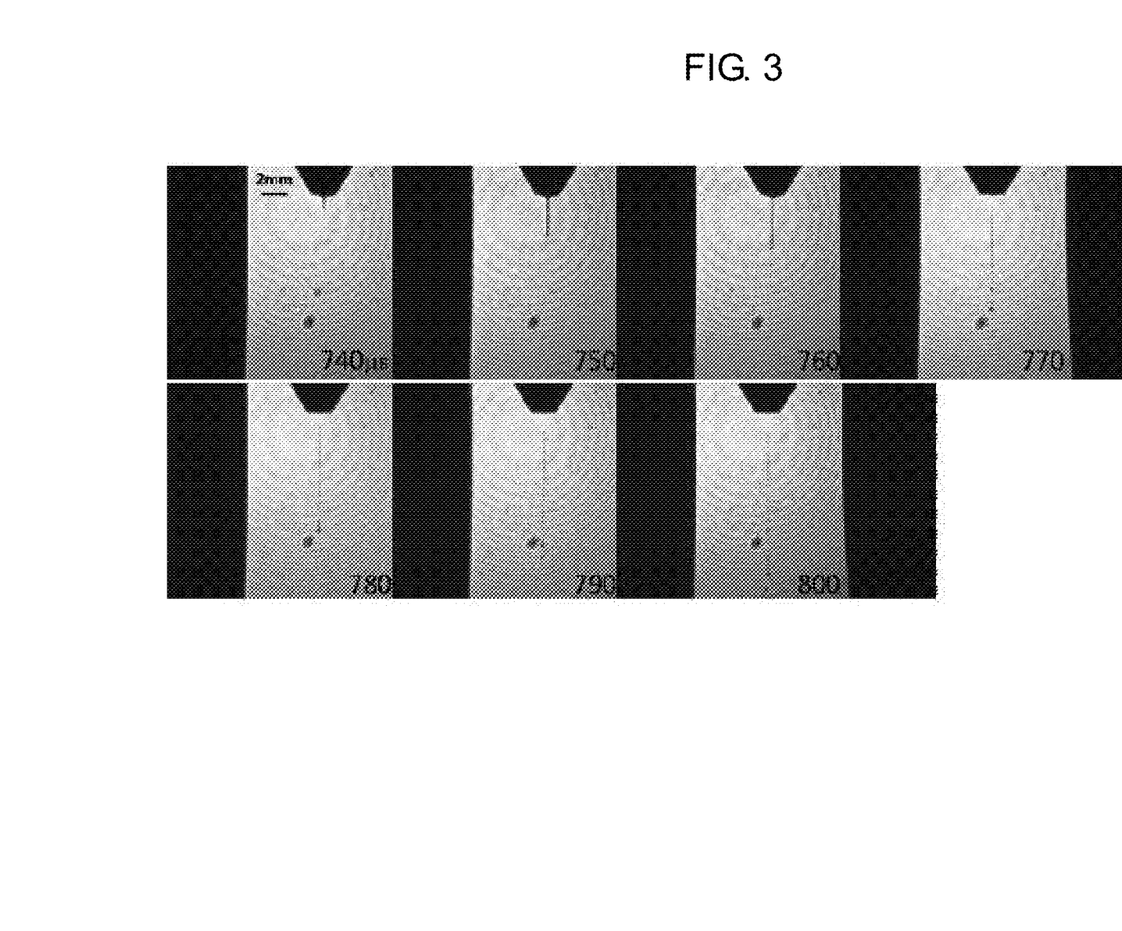
FIG. 3 is a sequence photo showing a process in which a drug solution is injected in the form of a liquid microjet by each time according to a preferred embodiment of the present invention.

FIG. 3 is a sequence photo showing a process in which a drug solution is injected in the form of a liquid microjet by each time according to a preferred embodiment of the present invention.

Figure 4:
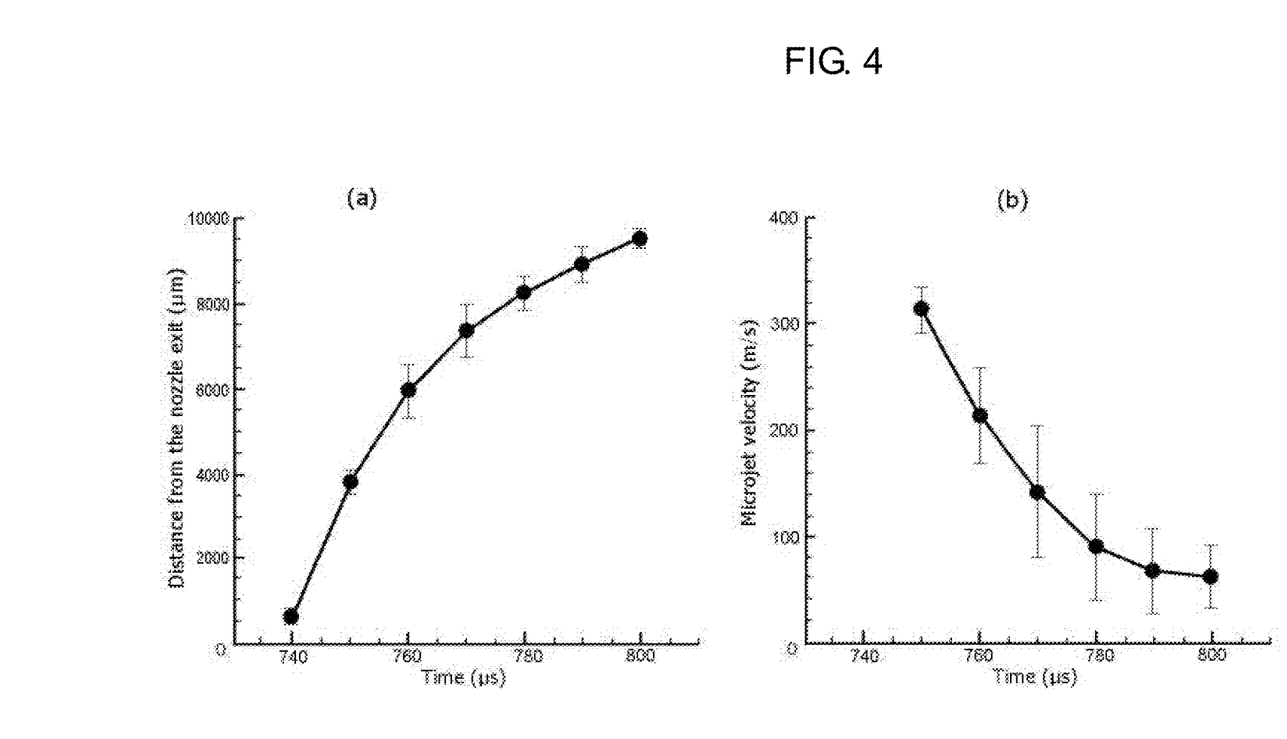
FIG. 4 is a graph showing the measurement results of the distance and velocity of a microjet from the nozzle exit over time in an experiment according to a preferred embodiment of the present invention.

FIG. 3 shows a result of irradiation of a laser beam having an energy of 100 mJ to the pressure-generating liquid. The traveling distance and injection velocity of the microjet from the nozzle exit over time can be found through the sequence photo of FIG. 3. In addition, FIG. 4 shows a graph of the measurement results of the distance and velocity of a microjet from the nozzle exit over time.

According to the present invention as described above, the microjet drug delivery system can reduce pain during the medical treatment and splashback, as well as is very excellent in stability and adjustability in the medical treatment. Also, the microjet drug delivery system enables the continuous supply and re-use of the drug solution. Thus, it is expected to be effectively substituted for a conventional drug delivery system using a syringe including a needle.

Meanwhile, the microjet drug delivery system of the present invention can be utilized in the form of a general syringe injecting a drug through the skin surface as described above, as well as can be very advantageously applied even in a medical treatment in which a drug is accurately administered into blood vessels or internal organs through its incorporation with an endoscope device and a laser therapy device.

For example, the endoscopic injection sclerotherapy (EIS), which is a sort of medical treatment method performed in the medical field, is a therapy which a special solution (i.e., curing agent) is injected into a vein to cause blood to be coagulated to occlude the blood vessels in order to prevent hemorrhage from occurring in the inner walls of the esophagus or the stomach or treat diseases such as varicose veins. In the above medical treatment, the microjet drug delivery system of the present invention can be desirably utilized in the injection of the curing agent.

In particular, as a medical equipment to remove a tumor occurring generally in blood vessels, internal organs or intervertebral disc in the medical field, a laser therapy device is widely used which allows a flexible optical fiber to guides the traveling path of a laser beam to irradiate the laser beam onto an internal affected site of a subject patient. The present invention may be used in such a fashion as to be coupled to a distal end of such a medical laser device Accordingly, a coupler for the laser therapy device, to which the technical concept of the present invention is applied, is mounted to a distal end of a laser fiber optic cable in the medical treatment and then is inserted into the internal affected site through a catheter or the like along with an endoscopic camera. Then, when a laser beam is irradiated onto the internal affected site, a drug solution can be accurately administered into the affected site.

Like this, in order for the drug delivery system of the present invention to be applied to a fiber optic coupler for a laser therapy device, the drug delivery system must be fabricated in a considerably small size. To this end, the drug delivery system may be fabricated in the form of an embodiment shown in FIG. 5.

In other words, according to the embodiment shown in FIG. 5, the microjet drug delivery system of the present invention is formed in a cylindrical shape in its entirety so that it can be mounted to a distal end of a fiber optic cable from which a laser beam is emitted in a medical laser therapy device. The inventive microjet delivery system includes a pressure chamber 10, an elastic membrane 30, a drug microchamber 20 and a micronozzle 40 so as to be constructed as a coupler product. Particularly, according to the embodiment of the microjet drug delivery system shown in FIG. 5, a portion abutting against a fiber optic cable 55 is processed in the shape of a semi-hemi-spherical lens so that a laser beam irradiated from the optical fiber can be refracted to be focused inside a pressure-generating liquid 100 contained in the pressure chamber 10. Thus, the inventive microjet delivery system can be easily mounted to an existing medical laser therapy device without a separate lens.

In the meantime, the microjet drug delivery system of the present invention may be implemented in the form of various products in a variety of industrial fields depending on the selection of one of ordinary skill in the art besides a general medical syringe device. In particular, as the interest in cosmetic treatment continues to grow, the present invention can also be preferably applied to a meso-therapy field which comes into spotlight as a promising cosmetic surgery method. For example, in the case of the obesity treatment as a representative filed of the meso-therapy, it is expected that the present invention will be applied to a cosmetic surgery method in which a fat-burning drug is injected into a bodily region where adipose cells are agglomerated so as to burn fat. In the cosmetic surgery method, three or more kinds of drugs are injected in a small dose.

Another desirable application field of the inventive microjet drug delivery system can be exemplified by the administration of an anaesthetic drug in the laser skin treatment. A laser hair or spot removal treatment commonly performed in a dermatology clinic employs an anaesthetic ointment to alleviate a pain due to laser heat. However, this anaesthetic ointment has a shortcoming in that it has no great effect in alleviation of a pain of a subject due to its poor skin penetration rate and is easily washed out during the treatment. As a very useful solution to a problem involved in such a conventional treatment method, the microjet drug delivery system of the present invention can be proposed. That is, the present invention may be implemented such that is constructed in the form of a patch unit which internally includes a local anaesthetic drug (for example, lidocaine), a pressure-generating liquid and an elastic membrane in a single product unit as a preferred embodiment of the present invention, and such that it employs an existing laser therapy device as the laser device. In the case of such a lidocaine patch, the microjet drug delivery system of the present invention may be preferably fabricated of a synthetic resin material so as to be used on a disposable basis by containing an anaesthetic drug dose therein, rather than an alloy material such as tungsten carbide used in the above-mentioned embodiment. More preferably, the inventive microjet drug delivery system may be implemented in the form of a product including an adapter so as to be mounted to an end tip of a medical laser device Furthermore, the present invention as constructed above is merely not limited to a drug delivery field, but may be applied to a variety of industrial fields. That is, according to the present invention, it is possible to effectively prevent a deterioration of a to-be-injected liquid due to laser heat in the injection of a trace amount of a liquid-phase ingredient in the form of a liquid microjet using a laser. Thus, it is expected that the present invention will also be extended and applied to other various fields through the positive utilization of its advantages. For example, it is expected that the present invention will be very preferably applied in a process in which stability of composition ingredients is very important and ingredient composition ratios is required to be maintained accurately as in the production of an ampoule of cosmetics or drugs.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. A microjet drug delivery system, comprising:
a pressure chamber having a predetermined sealed accommodating space formed therein and storing a pressure-generating liquid in the sealed accommodating space;
a drug microchamber disposed in proximity to and separately from the pressure chamber and configured to accommodate a drug solution in a predetermined accommodating space formed therein;
an energy-focusing device disposed separately and completely outside from the sealed accommodating space and configured to focus energy to the pressure-generating liquid stored in the pressure chamber to cause bubble growth due to vaporization of the pressure-generating liquid;
an elastic membrane disposed between the pressure chamber and the drug microchamber; and
a micronozzle connected to one side of the drug microchamber so as to be formed as a passageway through which the drug solution stored in the drug microchamber is injected to the outside in the form of a microjet.

2. The microjet drug delivery system according to claim 1, wherein the energy-focusing device is a laser generator that generates a laser beam and focusably irradiates the generated laser beam onto the pressure-generating liquid stored in the pressure chamber.

3. The microjet drug delivery system according to claim 1, wherein the energy-focusing device is an electrode that allows electrical energy to pass therethrough.

4. The microjet drug delivery system according to claim 1, wherein the pressure-generating liquid stored in the pressure chamber is any one selected from among water, alcohol and high-molecular compound of a gel or sol state.

5. The microjet drug delivery system according to claim 4, wherein the pressure-generating liquid comprises an electrolytic material dissolved therein.

6. The microjet drug delivery system according to claim 1, wherein the drug microchamber is connected to a drug reservoir having a drug solution contained therein so that the drug solution stored in the drug microchamber can be injected to the outside in the form of a microjet and then can be supplied with the drug solution from the drug reservoir.

7. The microjet drug delivery system according to claim 1, wherein the elastic membrane is made of a nitrile butadiene rubber (NBR).

8. The microjet drug delivery system according to claim 1, wherein the micronozzle comprises an exit having a coating layer formed on the inner peripheral surface thereof.

9. The microjet drug delivery system according to claim 2, wherein the pressure chamber is formed of a transparent material at one side surface thereof.

10. The microjet drug delivery system according to claim 9, wherein the one side surface of the pressure chamber formed of the transparent material is processed in the form of a lens.

11. An apparatus for injecting liquid in the form of a microjet, the apparatus comprising:

a pressure chamber having a predetermined sealed accommodating space formed therein and storing a pressure-generating liquid in the sealed accommodating space;

a microchamber disposed in proximity to and separately from the pressure chamber and configured to accommodate a to-be-injected drug solution in a predetermined accommodating space formed therein, the drug solution being injected in the form of a microjet;

an elastic membrane disposed between the pressure chamber and the microchamber and configured to partition the pressure chamber and the microchamber from each other;

a laser device comprising a laser generator for generating a laser beam and configured to focusably irradiate the generated laser beam onto the pressure-generating liquid stored in the pressure chamber, the laser device being disposed separately and completely outside from the sealed accommodating space of the pressure chamber; and a micronozzle formed as a passageway through which the to-be-injected drug solution stored in the drug microchamber is injected to the outside in the form of a microjet.

\* \* \* \* \*